(12) United States Patent
Peters

(10) Patent No.: US 6,508,807 B1
(45) Date of Patent: *Jan. 21, 2003

(54) COUPLING FOR MEDICAL CANNULAE

(76) Inventor: Joseph L Peters, Highfield, Little Widbury Lane, Ware Herts (GB), SG121 7AU ( * ) Notice: Subject to any disclaimer, the term of this patent is extended or adjusted under 35 U.S.C. 154(b) by 0 days.

This patent is subject to a terminal disclaimer.

(21) Appl. No.: 09/600,568

(22) PCT Filed: Jan. 20, 1999

(86) PCT No.: PCT/GB99/00178

§ 371 (c)(1),
(2), (4) Date: Sep. 8, 2000

(87) PCT Pub. No.: WO99/37356

PCT Pub. Date: Jul. 29, 1999

(30) Foreign Application Priority Data

Jan. 21, 1998 (GB) .............................. 9801261

(51) Int. Cl.⁷ .............................. A61M 25/16
(52) U.S. Cl. ...................... 604/533; 604/905
(58) Field of Search ................ 604/523, 905, 604/533, 534, 535, 537, 538, 247, 248, 249

(56) References Cited

U.S. PATENT DOCUMENTS

| 4,340,052 A | 7/1982 | Dennehey et al. |
| 4,405,312 A | 9/1983 | Gross et al. |
| 4,425,113 A | 1/1984 | Bilstad |
| 4,432,759 A | 2/1984 | Gross et al. |
| 4,473,369 A | 9/1984 | Lueders et al. |
| 4,631,056 A | 12/1986 | Dye |
| 5,000,739 A | 3/1991 | Kulisz et al. |
| 5,037,405 A | 8/1991 | Crosby |
| 5,531,695 A | 7/1996 | Swisher |
| 5,545,152 A | 8/1996 | Funderbunk et al. |
| 5,620,427 A | 4/1997 | Werschmidt et al. |
| 5,702,374 A | 12/1997 | Johnson |
| 5,830,195 A | 11/1998 | Peters et al. |

FOREIGN PATENT DOCUMENTS

| CH | 440871 | 1/1968 |
| CH | 670955 | 7/1989 |
| DE | 4318101 | 12/1994 |
| EP | 0031022 | 7/1981 |
| EP | 0098103 | 1/1984 |
| EP | 0217055 | 4/1987 |
| EP | 0227219 | 7/1987 |
| EP | 0248979 | 12/1987 |

(List continued on next page.)

Primary Examiner—Manuel Mendez
Assistant Examiner—Mark Nan
(74) Attorney, Agent, or Firm—Boyle, Fredrickson, Newholm, Stein & Gratz, S.C.

(57) ABSTRACT

A medical coupling for a cannulae includes a female member (1) with a body providing a hub (4) defining a socket (11), a valve section (5) with a valve actuator (15) slidable on the body, an internally splined sleeve (44) movable with the valve actuator, and a finger gripping section (5), and a male member (2) including a spiget (20) for engagement in the socket (11), a cap (21) with a screw thread for engagement with a thread (10) on the hub (4), and external splines (45) on the cap. When the spigot is inserted into the socket (11), the cap (21) is rotated onto the screw thread (10to hold them against being pulled apart, and the valve actuator is displaced to open the valve and to bring the splined sleeve (44) into locking engagement with the cap (31). A separate casing (30) is provided to form a sealed housing around the coupled parts, in a group of such couplings intended for use with different kinds of catheter, the spline arrangement on the cap (31) and in the sleeve (44) are different for each coupling to prevent the male member of one coupling being operatively connected to the female member of another coupling.

18 Claims, 2 Drawing Sheets

FOREIGN PATENT DOCUMENTS

| | | |
|---|---|---|
| EP | 0256640 | 2/1988 |
| EP | 0415665 | 3/1991 |
| EP | 0440101 | 8/1991 |
| EP | 0443868 | 8/1991 |
| EP | 0471574 | 2/1992 |
| EP | 0478495 | 4/1992 |
| EP | 0633038 | 1/1995 |
| EP | 0633039 | 1/1995 |
| EP | 0774270 | 5/1997 |
| GB | 2131510 | 6/1984 |
| GB | 2146405 | 4/1985 |
| GB | 2202747 | 10/1988 |
| WO | WO 83/00290 | 2/1983 |
| WO | WO 95/22369 | 8/1995 |
| WO | WO 98/02206 | 1/1998 |

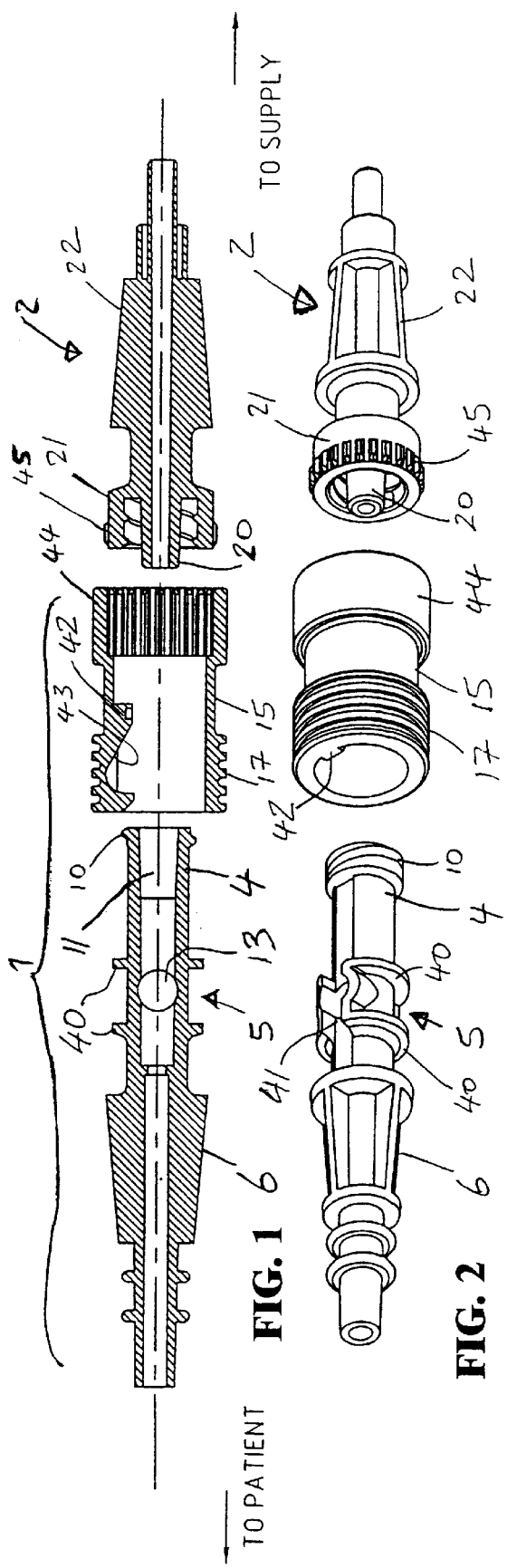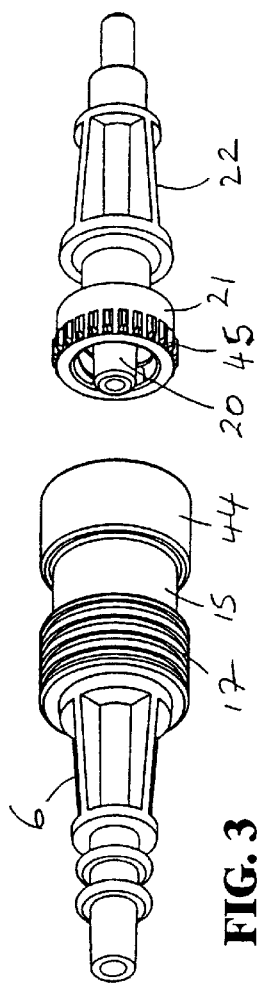
FIG. 1
FIG. 2
FIG. 3

COUPLING FOR MEDICAL CANNULAE

This invention relates to the field of medical equipment and in particular it is concerned with medical catheters and cannulae. An improved coupling device for connecting a cannula or catheter to a connection tube through which liquid to be administered to a patent is delivered, or fluid taken from a patient is collected, is described in my International Patent Application No. WO 98/02206. The invention described herein concerns modifications and further improvements to the coupling device described i the aforesaid application No. WO 98/02206.

Whereas the coupling device specifically described in WO 98/02206 has an internally splined sleeve carried by a male member of the device, and an externally splined collar is slidable on the female member for engaging and disengaging the splined sleeve to lock and unlock a cap which is rotatable to secure the male and female members in coupled cooperation, according to the modified construction of the invention described herein, external keying means such as splines are provided on the male member and the female member has a slidable part with complementary keying means on an inner surface. The keying means can conveniently be provided on the cap which forms part of the male member, and in the presently preferred embodiment, the cap is formed with a series of splines uniformly spaced around its exterior peripheral surface. An advantage of this construction is that the form of the male member is such that in visual appearance it may differ only very slightly, as a consequence of the provision of the splines, from male coupling members which have been in use on administration sets for a number of years and with which medical staff feel comfortable and are familiar. In the preferred embodiment the slide on the female member includes a collar with an extension sleeve having on its inner peripheral surface a series of splines complementary in arrangement and configuration to the splines of the cap.

Some catheters and cannulae of different kinds in use today and intended for different specific applications, such venous catheters, spinal catheters, nasal catheters, etc, are equipped with female coupling members adapted to fit with the identical forms of male coupling member with which the different types of administration sets intended for use with the respective catheters are supplied. As a result it is not impossible for a wrong administration set to be operatively connected to a catheter, especially if a patient is fitted with a number of catheters, and the consequences of such a mistake can be very serious and could even be fatal to the patient. The invention addresses this problem and as a solution it proposes a group or range of couplings for use with respective catheters adapted for different application to a patient, each coupling including a female member with a socket, a male member having a spigot for push fit engagement in the socket, a cap provided on one member and rotationally engageable with the other member to secure the spigot against disengagement from the socket, and a locking arrangement to lock the cap against rotation in the disengagement direction, e.g. as incorporated in the coupling devices according to WO 98/02206 and according to the present application, wherein each coupling of the group or range has complementary engaging means on the male and female members adapted to prevent the male or female member being operatively connected to a female or male member, respectively, of another coupling in the group or range.

Most conveniently, the complementary engaging means are provided by the locking arrangements and in the preferred form of coupling as described in detail herein the pattern of splines on the cap and within the sleeve is unique to each kind of catheter and associated administration set, so that any attempt to make an incorrect connection between an administration set and a catheter will be thwarted.

To assist a complete understanding of the invention a specific example of a coupling device in accordance with the invention is described in more detail below with reference to the accompanying drawings, in which:

FIG. 1 is an exploded axial section showing the main components of the coupling device;

FIG. 2 is an isometric view illustrating the main components shown in FIG. 1;

FIG. 3 is an isometric view of the male and female members;

Figure 4:
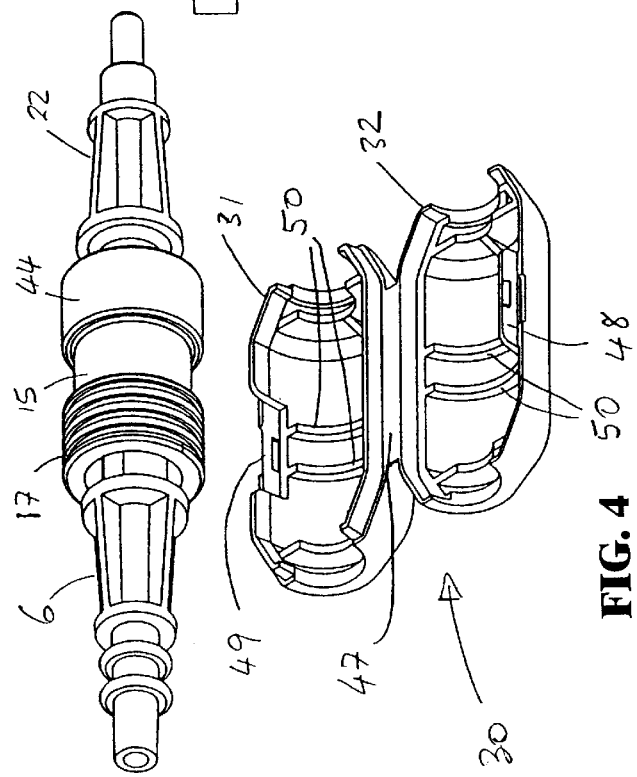
FIG. 4 is an isometric view showing the male and female members coupled and in combination with a capsule, illustrated in an open condition, for encasing the coupling device.

The catheter coupling device illustrated in the drawings comprises a female member 1 and a male member 2, the basic forms of which are substantially the same as in the coupling device described in WO 98/02206 to which reference can be made for further details. The female member 1, which is in use permanently attached to a cannula tube (not shown) includes a body having a hub section 4, a valve section 5 and a finger gripping section 6 configured to facilitate secure gripping with the fingers. The hub section 4 has a rim with a screw thread 10, and defines a frustoconical socket 11. Accommodated within the valve section 5 is a flexible-walled tube (not shown) having one end communicating with the socket 11 and the other end communicating with the bore of the cannula. A radial hole 13 in the body loosely receives a small ball (not shown) which rests against the flexible tube located within the body and which can be pushed inwardly against the tube thereby to pinch closed the fluid passage through the tube, the ball and tube thus constituting a valve device. For selectively pushing the ball inwardly to close the valve and releasing the ball to open the valve, a valve actuator 15 is slidably mounted on the body of the female member 1. The body has a pair of longitudinally spaced flanges 40 which are interrupted at a position aligned with the hole 13 so as to define a groove 41 for guiding the valve actuator 15 which has an inwardly directed key portion 42 which is engaged in the groove so that rotation of the valve actuator 15 is prevented. However, limited rotation of the valve actuator, e.g. through about 10° to 15° may be permitted as described in WO 98/02206. The key portion 42 includes a ramp surface 43 for effecting radial movement of the valve ball so that the valve is closed when the valve actuator is in a forward position (FIG. 3) and open when the actuator is in a rear position (FIG. 4). The forward end portion 17 of the actuator 15 includes circumferential grooves and is intended to assist adjustment of the actuator between its end positions, possibly by using a tool as described in WO 98/02206. The rear end of the valve actuator has a collar which is extended by an internally splined sleeve 44, the purpose of which is described later.

The male member 2 is conveniently made as a one piece moulding and includes a spigot 20 adapted to have a good friction fit in the socket 11. A cap 21 extends about the spigot and has an internal screw thread for cooperation with the thread 10 on the rim of the hub 4 for securing the spigot 20 against being pulled out of the hub socket 11. Behind the cap and spaced axially therefrom is a finger gripping section 22 to enable the male member 2 to be held firmly during connection to and disconnection from the female member 1. The external peripheral surface of the cap 21 is formed with a series of uniformly spaced splines 45 which are complementary in form to the splines provided within the sleeve 44. The splined sleeve 44 is arranged to cooperate with the splined cap 21 to lock the cap 21 against rotation relative to the female member and hence prevent unintentional unscrewing of the cap 21 and disconnection of the coupling. An axial bore through the male member extends from the free end of the spigot to a rear connection piece by means of which the member is fixedly and sealingly attached to a tube, e.g. a delivery tube of an administration set.

Figure 5:
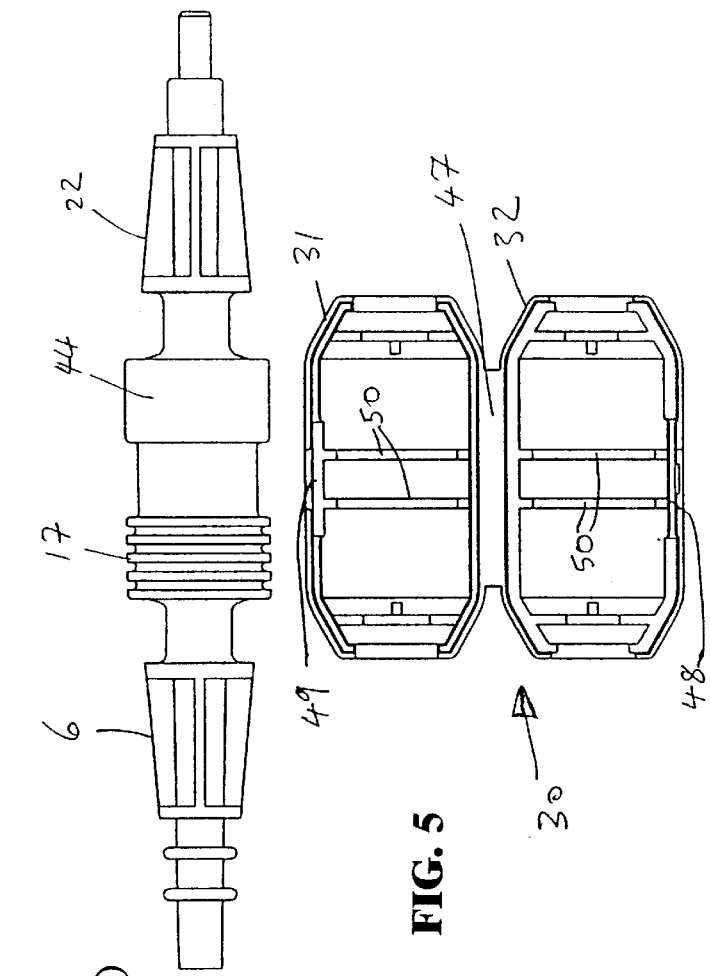
FIG. 5 is a plan view of the assembled coupling device in combination with the open capsule.

Holding the male and female members 1, 2 by their respective gripping sections 6,22 the members are brought together axially so that the spigot 20 enters the hub socket 11, the valve actuator 15 being initially in the forward position (FIG. 3) so that the valve is closed. The members 1,2 are then relatively rotated to screw the cap 21 onto the rim of the hub 4 and to ensure that the spigot 20 is firmly and sealingly engaged in the hub socket 11. The valve actuator 15 is slid rearwardly along the body of the female member 1 so that the splined sleeve 44 passes over the splined cap 21. The ends of the splines on the sleeve and/or cap are shaped so that the valve actuator 15 is rotated slightly if necessary to bring the splines into correct angular orientation for engagement, as described in WO 98/02206. When the splined sleeve 44 covers the cap 21 as shown in FIGS. 4 and 5, the valve is fully opened an the cap is securely locked against rotation and hence prevented from being unscrewed from the hub 4.

For additional security and protection against infection, an outer capsule or casing 30 is applied over the coupled members 1,2 to encase the parts of these members located between the gripping sections 6,22. The casting has two parts 31,32 integrally connected along one edge by a living hinge 47. A latch tongue 48 on one part is arranged to engage with a snap fit in a complementary latch socket 49 in the other part for securing the two parts together in the closed condition. Other details of the casing may be as described in WO 98/02206. It may be noted, however, that the casing 30 is longitudinally symmetrical enabling it to be fitted either way round on the assembled coupling. For this reason the axial distance separating the cap 12 from the gripping section 22 is substantially equal to the distance between the gripping section 6 and the forward end of the valve actuator 15 when the valve actuator is in the rearmost position. Ribs 50 within the casing parts 31, 32 are so positioned that they engage the sleeve 44 if attempt is made to fit the casing 30 before the valve actuator 15 has been displaced to lock the cap 21 and open the valve, so that it is then not possible to close the casing.

The coupling device described ha all the advantages of the coupling device of WO 98/02206 and in addition has the advantage that the male member is not substantially different to male members to known couplings.

The invention also resides in a range of such couplings for use with different kinds of catheter, each coupling being substantially as described above, but the couplings having different spline arrangements in terms of numbers of splines, size of splines and/or spatial orientation of splines so that the male members are in effect coded to enable their use with only one predetermined kind of catheter. Additionally or alternatively other parts of the male and female members which are arranged to cooperate may be adapted to prevent a male member of one coupling being operatively coupled to the female member of another coupling of the range or group. For example, the couplings may have male spigot and female socket shapes and/or dimensions which differ from one coupling to the next so that the spigot of the male member of one coupling will not fit with the socket of the female member of a different coupling. Of course a small spigot will be insertable into a socket intended for a larger spigot but in that case a sealed connection will not be obtained and if attempt is mistakenly made to complete such an incorrect coupling it will be immediately signalled by leakage of fluid from the coupling. With such a construction safety can be ensured by the couplings intended for vascular, i.e. intravenous or arterial catheters having the smallest size spigot and socket, couplings intended for intrathecal (spinal) administration having the next larger size, followed by couplings intended for nasal and gastro cannulae and couplings intended for use with tubes inserted into the chest having the largest size spigot and socket, for example.

What is claimed is:

1. A coupling for a medical cannula comprising a female member (1) having a socket (11), a male member (2) having a spigot (20) engageable with a push fit into the socket (11), a cap (21) attached to one member and rotationally engageable with the other member to secure the spigot against disengagement from the socket, and a locking arrangement to lock the cap (21) against rotation in the direction of disengagement from said other member, characterised in that the locking arrangement comprises an external keying configuration (45) on the male member (2) and a slide (15) having a complementary keying configuration on an inner surface thereof, the slide being movable on the female member to bring the keying configurations into engagement and thereby lock the cap (21) against rotation in the disengagement direction.

2. A coupling according to claim 1, wherein the external keying configuration (45) is carried by the cap (21).

3. A coupling according to claim 1, wherein the slide (15) includes a sleeve (44) with the inner keying configuration provided on the inner peripheral surface thereof.

4. A coupling according to claim 1, wherein the external keying configuration and/or the inner keying configuration comprises a series of uniformly spaced splines.

5. A coupling according to claim 1, wherein the cap (21) is fixedly mounted on the male member (2) and is externally splined, and the slide (15) comprises an internally splined sleeve (44) for engagement with the splined cap.

6. A coupling according to claim 5, wherein the slide (15) is capable of rotation through a limited angle substantially less than a full revolution for bringing the splines into alignment during engagement of the slide (15) with the cap (21).

7. A coupling according to claim 6, wherein the ends of the splines are shaped to bring about automatically any rotation of the slide (15) necessary to allow locking engagement of the slide (15) with the cap (21).

8. A coupling according to claim 1, wherein the female member includes a valve having a valve actuator, the slide being movable with the valve actuator.

9. A coupling according to claim 8, wherein axial movement of the valve actuator to open the valve engages the locking arrangement.

10. A male coupling member for a medical cannula coupling, comprising a spigot (20) for push fit engagement in a socket of a female coupling member, an internally screw-threaded cap (21) attached to the spigot for threaded engagement with the female member to secure the spigot (20) against disengagement from the socket, characterised in that an external keying means (45) is provided on the cap for engagement by locking part of the female member to lock the cap against rotation in the disengagement direction.

11. A male coupling member according to claim 10, wherein the external keying means comprises a series of splines (45) uniformly distributed around an outer peripheral surface of the cap.

12. A female coupling member for a medical cannula coupling, comprising a hub (4) a socket (11) for receiving a spigot of a male member engageable therein with a push fit, and means (10) on the hub (4) engageable by an internally screw-threaded cap of the male member for securing the spigot against disengagement from the socket (11), characterised in that a locking part (15) slidable relative to the hub includes a sleeve (44) provided with internal keying means for engagement with complementary keying means (45) provided on the exterior of the cap of the male member for locking the cap against rotation in the disengagement direction.

13. A female coupling according to claim 12, wherein the internal keying means comprises a series of splines uniformly spaced around the inner peripheral surface of the sleeve (44).

14. A group or range of medical couplings for use with catheters adapted for different application to a patient, each coupling of the group or range including a female member (1) having a socket (11), a male member (2) having a spigot (20) for push fit engagement in the socket (11), a cap (21) provided on one member and rotationally engageable with the other member to secure the spigot against disengagement from the socket, and a locking arrangement to lock the cap (21) against rotation in the disengagement direction, characterised in that each coupling in the range or group has complementary engaging means (44,45) on the male and female members adapted to prevent the male or female member being operatively connected to a female or male member, respectively, of any other coupling in the group or range of couplings.

15. A group or range of couplings according to claim 14, wherein the locking arrangements of the couplings differ from each other to prevent male and female members of respective couplings being operatively connected to one another.

16. A group or range of couplings according to claim 15, wherein the locking arrangement of each coupling includes a slide (15) with keying means (44) movable into and out of engagement with complementary keying means (45) carried by the cap (21), the keying means being arranged to prevent the keying means (44) on the slide being moved into operative engagement with the keying means (45) carried by the cap (21) of another coupling in the group or range of couplings.

17. A group or range of couplings according to claim 14, wherein the male spigot and female socket of each of the couplings are of different size and/or shape to those of the other couplings.

18. A group or range of couplings according to claim 14, wherein each coupling is defined in claim 1.

* * * * *